(12) United States Patent
Serov et al.

(10) Patent No.: US 10,864,460 B2
(45) Date of Patent: Dec. 15, 2020

(54) GRAPHENE-BASED INORGANIC-ORGANIC HYBRID MATERIALS AND SEPARATION OF RACEMIC MIXTURES

(71) Applicants: Alexey Serov, Albuquerque, NM (US); Plamen B Atanassov, Santa Fe, NM (US); Nikolai Kalugin, Albuquerque, NM (US); Liliya V Frolova, Socorro, NM (US)

(72) Inventors: Alexey Serov, Albuquerque, NM (US); Plamen B Atanassov, Santa Fe, NM (US); Nikolai Kalugin, Albuquerque, NM (US); Liliya V Frolova, Socorro, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 564 days.

(21) Appl. No.: 15/515,960

(22) PCT Filed: Sep. 30, 2015

(86) PCT No.: PCT/US2015/053074
§ 371 (c)(1),
(2) Date: Mar. 30, 2017

(87) PCT Pub. No.: WO2016/054129
PCT Pub. Date: Apr. 7, 2016

(65) Prior Publication Data
US 2017/0253489 A1    Sep. 7, 2017

Related U.S. Application Data

(60) Provisional application No. 62/057,313, filed on Sep. 30, 2014.

(51) Int. Cl.
*C07D 207/08* (2006.01)
*C01B 32/196* (2017.01)
(Continued)

(52) U.S. Cl.
CPC .......... *B01D 15/08* (2013.01); *B01J 20/205* (2013.01); *B01J 20/22* (2013.01); *B01J 20/286* (2013.01);
(Continued)

(58) Field of Classification Search
CPC ........ B01J 20/22; B01J 20/261; B01J 20/262; B01J 20/265; B01J 20/28014;
(Continued)

(56) References Cited

U.S. PATENT DOCUMENTS 5,200,473 A * 4/1993 Jeanneret-Gris ......... B01J 45/00
521/30
6,201,158 B1 * 3/2001 Li ........................... C07C 29/42
546/344

(Continued)

OTHER PUBLICATIONS

Jiang et al. Design of advanced porous graphene materials: from graphene nanomesh to 3D architectures. Nanoscale, 2014, 6, 1922-1945. (Year: 2014).*

(Continued)

*Primary Examiner* — Katherine Zalasky McDonald
(74) *Attorney, Agent, or Firm* — Gonzales Patent Services; Ellen M. Gonzales

(57) ABSTRACT

A variety of inorganic-organic hybrid materials and various methods for preparing and using the same are described. The hybrid materials are graphene or graphitic materials populated with organic molecules and may have a variety of surface defects, pits or three-dimensional architecture, thereby increasing the surface area of the material. The hybrid materials may take the form of three dimensional graphene nanosheets (3D GNS). If the organic molecules are enantiospecific molecules, the hybrid materials can be used for chiral separation of racemic mixtures.

12 Claims, 4 Drawing Sheets

GO (exfoliated)    + SiO₂    Reduction    HF Leaching

(51) Int. Cl.

| | | |
|---|---|---|
| *C01B 32/182* | (2017.01) | |
| *B01J 20/20* | (2006.01) | |
| *B01J 20/28* | (2006.01) | |
| *B01J 20/22* | (2006.01) | |
| *B01J 20/286* | (2006.01) | |
| *B01J 20/30* | (2006.01) | |
| *B01J 20/32* | (2006.01) | |
| *B01D 15/08* | (2006.01) | |
| *C07C 51/47* | (2006.01) | |
| *G01N 30/02* | (2006.01) | |
| *G01N 30/14* | (2006.01) | |
| *G01N 30/62* | (2006.01) | |
| *C01B 32/21* | (2017.01) | |

(52) U.S. Cl.
CPC ..... *B01J 20/28014* (2013.01); *B01J 20/3064* (2013.01); *B01J 20/3251* (2013.01); *C01B 32/182* (2017.08); *C01B 32/196* (2017.08); *C01B 32/21* (2017.08); *C07C 51/47* (2013.01); *C07D 207/08* (2013.01); *G01N 30/02* (2013.01); *G01N 30/14* (2013.01); *G01N 30/62* (2013.01); *C07B 2200/09* (2013.01); *G01N 2030/027* (2013.01); *G01N 2030/143* (2013.01); *G01N 2030/146* (2013.01); *G01N 2030/621* (2013.01); *G01N 2030/623* (2013.01)

(58) Field of Classification Search
CPC ........ B01J 20/281; B01J 20/286; B01J 20/29; B01J 20/285; B01J 20/32; B01J 20/3206; B01J 20/3208; B01J 20/321; B01J 20/3231; B01J 20/3242; B01J 20/3244; B01J 20/3246; B01J 20/3248; B01J 20/3251; B01J 20/3255; B01J 20/3285; B01J 20/20; B01J 20/205; C01B 32/15; C01B 32/158; C01B 32/18; C01B 32/182; C01B 32/194; C01B 32/21
See application file for complete search history.

(56) References Cited

U.S. PATENT DOCUMENTS

| | | | | |
|---|---|---|---|---|
| 2011/0299081 | A1* | 12/2011 | Manka | G01N 21/211 356/364 |
| 2014/0100373 | A1* | 4/2014 | Kawabata | C07D 487/04 548/302.7 |
| 2015/0210640 | A1* | 7/2015 | Ikuma | C07D 403/12 514/233.5 |
| 2016/0130148 | A1 | 5/2016 | Serov et al. | |

OTHER PUBLICATIONS

Gubitz et al. Resolution of the enantiomers of barbiturates on a new chiral amino alcohol phase by CLEC. Quimica Analitica (1993) 12:45-47. (Year: 1993).*

Hauser et al. Functionalized graphene as a gatekeeper for chiral molecules: An alternative concept for chiral separation. Angew. Chem. Int. Ed. (2014) 53, 9957-9960. (Year: 2014).*

Huh et al. UV/Ozone-oxidized large-scale graphene platform with large chemical enhancement in surface-enhanced raman scattering. ACS Nano, vol. 5, No. 12 (2011) 9799-9806. (Year: 2011).*

Surface-modified threedimensional graphene nanosheets as a stationary phase for chromatographic separation of chiral drugs, Scientific Reports (2018) 8:14747.

* cited by examiner ed. Sep. 30, 2014,# GRAPHENE-BASED INORGANIC-ORGANIC HYBRID MATERIALS AND SEPARATION OF RACEMIC MIXTURES

CROSS-REFERENCE TO RELATED APPLICATIONS

The following application claims benefit of U.S. Provisional Application No. 62/057,313, filed Sep. 30, 2014, which is hereby incorporated by reference in its entirety.

BACKGROUND

Many compounds that are important for biology and medicine are chiral, i.e. they have structural asymmetry and demonstrate optical activity (rotation of polarization plane of propagating electromagnetic radiation). For example, about 40% of pharmaceutical drugs are chiral compounds, and only approximately 25% are used in the form of pure enantiomers. Quite frequently, pharmacological efficiency is restricted to only one of the enantiomers (eutomer), and in some cases the "mirror images" of efficient drugs (distomers) demonstrate toxicity or undesirable medical side effects. Furthermore, even if the distomers are non-toxic, they have to be metabolized by the patient, which represents an unnecessary burden to patient's metabolic system. Therefore, the availability of chirally pure drugs is one of the most important problems of modern pharmaceutics.

Ideally, the best solution to the problem would be direct enantioselective synthesis of chiral drugs. Unfortunately, in many cases this approach is very expensive, and, in a majority of cases, impossible. Usually, synthesis provides racemic mixtures of compound, containing an approximately 50:50% mixture of both enantiomeric forms. Therefore, the separation of enantiomers is the most realistic solution of the problem.

The issue of chiral separation is very important not only for the pharmaceutical industry, but also as an analytical tool for controlling the efficiency of synthesis and the quality/properties of the synthesized products, monitoring the racemization processes, investigation of pharmacokinetics, and other applications. Typical methods of chiral separation include functional crystallization and formation of diastereometric pairs followed by recrystallization. In some cases separation procedures may include the use of enzymes. Recently, capillary electrophoresis and chromatographic techniques (and high performance liquid chromatography (HPLC) in particular) became to be more and more popular method of chiral separation. See, e.g., L. A. Nguyen, H. He, Ch. Pham-Huy, Chiral Drugs: An Overview, *International Journal of Biomedical science*, 2(2) 85-100, 2006; W. H. Porter, Resolution of chiral drugs, *Pure & Appl. Chem.*, Vol. 63, No. 8, pp. 11 19-1 122, 1991; Chiral Separation Techniques, A Practical Approach, $3^{rd}$ edition, Ed. By G. Subramanian, Wiley-VCH, 2007; Chiral Separations: Methods and Protocols, Ed. By G. Gubitz and M. G. Schmid, Humana Press, 2004; and Chromatographic Chiral Separations, Ed. By M. Zief and L. J. Grane, Marcel Dekker, 1988.

However, each of these methods comes with its own drawbacks and burdens including difficulty and expense. Accordingly, novel methods and materials for chiral separations are desperately needed.

SUMMARY

The present disclosure provides a variety of inorganic-organic hybrid materials and methods for using the same. According to a general embodiment, the hybrid materials are graphene or graphitic materials populated with organic molecules. According to a further embodiment, the hybrid materials have a variety of surface defects, pits or three-dimensional architecture that increases the surface area of the material. According to a still further embodiment, the hybrid materials include three dimensional graphene nanosheets (3D GNS) that take the form of non-contiguous graphene mono or multi-layers comprising a plurality of defects and pores. Alternatively, the 3D GNS may be thought of as disordered graphene mono or multi-layered walls surrounding pores formed from the removal of a plurality of sacrificial particles. According to a still further embodiment the organic molecules are enantiospecific molecules that enable the hybrid materials to be used for chiral separation of racemic mixtures. Accordingly, the present disclosure further provides methods for chiral separation of racemic mixtures using the inorganic-organic hybrid materials disclosed herein.

DETAILED DESCRIPTION

Figure 1:
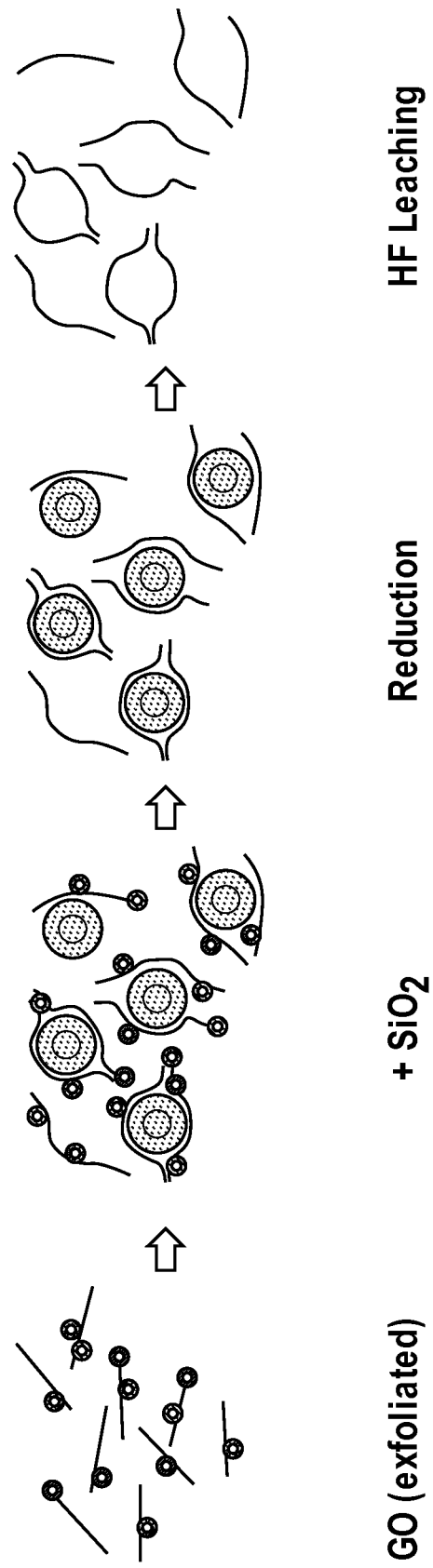
FIG. 1 is a schematic illustration of the steps of a method for producing 3D graphene structures according to an embodiment of the present disclosure.

According to an embodiment the present disclosure provides novel graphene-based inorganic-organic hybrid materials useful for a variety of applications including, but not limited to, detection and separation techniques, catalysis, concentration of diluted solutions, desalination, wastewater treatment, gas adsorption etc. According to a specific embodiment, these hybrid materials can be used as the stationary phase for HPLC-based chiral separation of chemical compounds.

In general, the hybrid materials of the present disclosure are formed by chemically modifying the surface of graphene or graphitic materials with organic molecules. According to an embodiment, the hybrid materials have a variety of surface defects, pits or three-dimensional architecture that increases the surface area of the material. According to a further embodiment, the hybrid materials include three dimensional graphene nanosheets (3D GNS) that take the form of non-contiguous graphene mono or multi-layers incorporating numerous defects and pores. According to a still further embodiment the organic molecules are enantiospecific molecules that enable the hybrid materials to be used for chiral separation of racemic mixtures.

For the purposes of the present disclosure the term "mono-layer graphene" refers to a flat, 2-dimensional sheet, or platelet, formed from a single layer of carbon atoms arranged in a hexagonal pattern. A graphene "multi-stack" or "few-layer graphene" is formed from multiple individual layers of graphene sheets stacked on top of each other. As an analogy, a graphene mono-layer might be thought of as a sheet of paper, a graphene "multi-stack" (or few-layer graphene) as several sheets of paper stacked on top of each other. For the purposes of the present disclosure, anything with a thickness of greater than 50 graphene layers will be considered graphite, while 50 or fewer graphene layers is considered graphene. Accordingly, graphene structures may have a thickness of 50 or fewer layers, 20 or fewer layers, 10 of fewer layers, 6 or fewer layers, 3 or fewer layers, 2 or fewer layers, or only 1 layer of graphene.

Accordingly, while a three-dimensional graphene-like structure may be formed by manipulating a single contiguous sheet or multiple layers of contiguous sheets of graphene in the same way a sheet or a few layered sheets of paper can be crumpled, folded, bent, or otherwise manipulated to form a three-dimensional structure, the present disclosure also contemplates non-contiguous three dimensional graphene structures having one or more voids that are defined and separated by graphene walls and wherein the walls of the structures are formed from fewer than 50 layers of graphene. It is important to note that, in this embodiment, the walls and overall structure are not formed from a manipulated preformed single contiguous sheet (or stack of sheets), and, in fact, in "non-contiguous" embodiments, the overall structure could not be "unrolled," or "uncrumpled," in order to form a single contiguous sheet (as distinguished from, for example, carbon nanotubes, which if unrolled, would form a single contiguous sheet).

For the purposes of the present disclosure a "graphene wall" is a section of hexagonally arranged carbon atoms that forms the physical structure of the final non-contiguous material. According to some embodiments the graphene wall may consist of a single-layer of hexagonally arranged carbon atoms or fewer than 3, fewer than 6, fewer than 10, fewer than 20 or fewer than 50 layers of single-layer sheets. As explained in more detail below, some or all of the graphene walls in a particular embodiment may be more "string-like" in appearance. However, unlike the graphene sheets that have been previously described, which are simply flat platelets, some or all of the graphene sheets or walls (and/or portions thereof) formed by the methods described herein may be curved, rounded, or otherwise non-planar in shape. Furthermore, various walls may branch or connect with other walls to form the complex 3D morphology described herein. Accordingly, it will be understood that while the wall in general may be referred to as having a specific thickness (i.e., 1, 5, or 10 layers of graphene sheets) some or all of the wall junctions i.e., regions where one or more "walls" connect, may be viewed as having a greater thickness, even though the general structure is considered to have an overall wall thickness of the 1, 5, or 10 layers, based on the thinnest section of the wall.) Accordingly, for the purposes of the present disclosure, the thickness of a particular graphene wall is determined by the area in which the least number of carbon atoms can be measured, (i.e., the thinnest portion of the wall). According to some preferred embodiments, the graphene walls may have a thickness of between 6 and 10 graphene layers. It will be understood that while no particular wall will have a thickness of more than 50 layers, because the structure may contain many walls and many voids, the overall structure itself may have a much, much larger diameter.

According to an embodiment, the 3D-GNS of the present disclosure are produced using a sacrificial support-based method wherein one or more graphene precursors, such as graphene oxide, or other carbons are mixed with sacrificial particles. The precursor/sacrificial support mixture is then reduced to produce a hybrid graphene nanosheets that incorporates the sacrificial particles as distinct elements within the nanosheets. The sacrificial particles are then removed, resulting in a "three-dimensional" graphene nanosheet incorporating a variety of defects and pores (or voids) resulting from the removal of the sacrificial particles. See e.g., the first three steps of the exemplary synthesis route shown in FIG. 1. While it will be understood from further reading that the methods described herein enable the production of pores of virtually any size, shape, diameter, and density, according to various specific embodiments, the pores in question may have an average pore diameter of between 5 and 250 nm.

For the purposes of the present disclosure, the term "sacrificial particle" is intended to refer to a particulate material that is mixed with the graphene oxide and included during the graphene nanosheet synthesis process in order to provide temporary structure but which is mostly or entirely removed from the final product.

According to a specific embodiment, graphene oxide is produced using a modified Hummers method (see e.g., W. S. Hummers, R. E. Offeman, *J. Am. Chem. Soc.,* 1958, 80, 1339). In general, graphite flakes are added to sulfuric acid ($H_2SO_4$) and potassium permanganate ($KMnO_4$) solution under continuous stirring over a heated water bath, followed by a slow addition of $H_2O_2$ (30%) to yield graphene oxide (GOx).

According to various embodiments of the present disclosure, the graphene oxide and sacrificial particles are mixed under suitable conditions. For example, the graphene oxide and sacrificial particles may be mixed in solution and/or using the mechano-chemical synthesis means as described below, in order to coat, deposit, impregnate, infuse, or similarly associate the graphene oxide with the sacrificial support. For the sake of simplicity, unless otherwise specified, the term "coat" is used herein as a catchall phrase to refer to any type of physical association, whether or not the "coating" is complete or partial and whether exclusively external or both internal and external. The graphene/sacrificial particle mixture is dried, if necessary, and reduced (for example via thermal or chemical reduction), and the sacrificial support removed, resulting in a porous, irregularly shaped, three-dimensional graphene nanosheet. It will be understood that in contrast synthesis mechanisms that rely on templating to reproduce the very specific, typically organized, structure of a monolithic block template, the sacrificial support method of the present disclosure results in a disorganized final structure that is determined by the random placement of the sacrificial support particles in the graphene precursor/sacrificial support mixture.

According to some embodiments, the graphene precursor(s) and sacrificial support particles may be mixed together under aqueous conditions using known solvents such as water, alcohols, or the like and using various known mechanical mixing or stirring means under suitable temperature, atmospheric, or other conditions as needed in order to enable or produce the desired degree of dispersion of sacrificial particles within the mixture. It should be understood that because the final morphology of the 3D-GNS material is determined by the size, shape, and relative placement of the sacrificial particles within the mixture, different applications may require or benefit from different ratios or degrees of dispersion of the particles within the graphene oxide-sacrificial particle mixture. For example, clumping of the particles (i.e. less even dispersion) with in the mixture could result in larger pores and a higher degree of irregularity, which could be desirable for some applications, which more evenly dispersed particles could result in a more even distribution of pores and more consistent pore sizes, which could be desirable in other applications. Suitable mixing means include, for example, use of an ultrasound bath, which also enables dispersion of the sacrificial support particles.

Alternatively or additionally, the graphene precursor(s) and sacrificial particles may be mixed together using mechano-chemical synthesis techniques such as high energy ultrasonic power or ball-milling.

It will be appreciated that the presently disclosed methods enable the production of graphene nanosheets having highly predictable morphology. Specifically, by selecting the ratio of sacrificial support particles to graphene oxide and the size, shape, and even porosity of the sacrificial template particles, it is possible to control, select, and fine-tune the internal structure of the resulting 3D graphene nanosheet material. In essence, the disclosed method enables the production of 3D nanosheet having as convoluted and tortuous a morphology as desired. For example, a highly porous open-structure "sponge-like" material may be formed by using larger sacrificial template particles, while a highly convoluted, complex internal structure may be formed by using smaller, more complexly shaped, sacrificial particles, including for example, sacrificial particles of different shapes and/or sacrificial particles which are themselves porous. Moreover, the "density" of the 3D material can be selected by altering, for example, the ratio of sacrificial particles to graphene precursor materials, the shape of the template particles (i.e. how easily they fit together), or other factors. Thus, it should be appreciated that while the overall final structure of the material is disorganized and unpredictable, various aspects of the structure, such as the density, pore size, degree of porosity, and the like can be specifically controlled.

Accordingly, it will be appreciated that the size and shape of the sacrificial particles may be selected according to the desired shape(s) and size(s) of the voids within the final product. Specifically, it will be understood that by selecting the particular size and shape of the support particles, one can produce a material having voids of a predictable size and shape. For example, if the template particles are spheres, the 3D material will contain a plurality of spherical voids having the same general size as the spherical particles.

As a specific example, assuming there is no alteration in the size of the particle caused by the synthesis method, in an embodiment where particles having an average diameter of 20 nm is used, the spherical voids in the final product will typically have an average diameter of approximately 20 nm. (Those of skill in the art will understand that if the diameter of the particle is 20 nm, the internal diameter of the void in which the particle resided will likely be just slightly larger than 20 nm and thus the term "approximately" is used to account for this slight adjustment.)

Accordingly it will be understood that the sacrificial particles may take the form of any two- or three-dimensional regular, irregular, or amorphous shape or shapes, including, but not limited to, spheres, cubes, cylinders, cones, etc. Furthermore, the particles may be monodisperse, or irregularly sized.

It will be further understood that because the material is formed using a sacrificial support technique, where the sacrificial material can be, for example, "melted" out of the supporting materials using acid etching or other techniques, the resulting material can be designed to have a variety of variously shaped internal voids which result in an extremely high internal surface area that can be easily accessed by, for example, gasses or liquids that are exposed to material (for example, in a fuel cell). Furthermore, because the size and shape of the voids is created by the size and shape of the sacrificial particles, materials having irregular and non-uniform voids can easily be obtained, simply by using differently shaped sacrificial particles and/or by the non-uniform distribution of sacrificial materials within the graphene precursor/sacrificial particle mixture. Furthermore, the sacrificial-support based methods of the present disclosure may produce catalysts having, for example, a bi-modal (or even multi-modal) pore distribution either due to the use of differently sized sacrificial particles or where a first smaller pore size is the result of removal of individual particles and thus determined by the size of the sacrificial particles themselves and a second, larger, pore size is the result of removal of agglomerated or aggregated particles. Accordingly, it will be understood that the method described herein inherently produces a material having a unique morphology that would be difficult, if not impossible, to replicate using any other technique.

As stated above, according to various embodiments, sacrificial particles of any size or diameter may be used. In some preferred embodiments, sacrificial particles having a characteristic length/diameter/or other dimension of between 1 nm and 100 nm may be used, in more preferred embodiments, sacrificial particles having characteristic length/diameter/or other dimension of between 100 nm and 1000 nm may be used and in other preferred embodiments, sacrificial particles having characteristic length/diameter/or other dimension of between 1 mm and 10 mm may be used. It should also be understood that the term "sacrificial particle" is used herein as a term of convenience and that no specific shape or size range is inherently implied by the term "particle" in this context. Thus while the sacrificial particles may be within the nanometers sized range, the use of larger or smaller particles is also contemplated by the present disclosure.

According to some embodiments, the sacrificial particles may themselves be porous. Such pores may be regularly or irregularly sized and/or shaped. The use of porous sacrificial particles enables the graphene precursor(s) to intercalate the pores, producing even more complexity in the overall three-dimensional structure of the resulting catalyst.

It will be appreciated that the sacrificial particles may be synthesized and mixed (or coated, or infused, etc.) in a single synthesis step or the graphene precursor(s) may be mixed with pre-synthesized (whether commercially purchased or previously synthesized) sacrificial particles.

Of course it will be appreciated that given the various conditions that the sacrificial template will be subjected to during the synthesis process, it is important to select a sacrificial material which is non-reactive to the catalytic materials under the specific synthesis conditions used and the removal of which will not damage the final material. For example, if the supporting material is to be used as an active support (i.e. a support which can synergistically promote the main catalyst), it is important that the method(s) used to remove the sacrificial particles not damage the support's active sites.

Silica is a material known to easily withstand the conditions described herein while remaining inert to a variety of catalytic materials including the metals described herein. Furthermore, silica can be removed using techniques that are harmless to graphene materials. Thus, silica is considered to be a suitable material from which the sacrificial template particles can be made. According to some specific embodiments, 20 nm diameter spheres formed from mesoporous silica can be used. In this case the templating involves intercalating the mesopores of the silica template particles and the resulting material typically contains pores in the 2-20 nm range. In one particular embodiment, the silica template is commercially available Cabosil amorphous silica (400 $m^2/g^{-1}$). Furthermore, selecting a different type of silica can also alter the shape and size of the pores in the final 3D-GNS product. Those of skill in the art will be familiar with a variety of silica particles that are commercially available, and such particles may be used. Alternatively, known methods of forming silica particles may be employed in order to obtain particles of the desired shape and/or size.

However, while many of the examples herein utilize silica for the templating materials, it will be appreciated that other suitable materials may be used including, but are not limited to, zeolites, aluminas, clays, magnesia and the like.

As stated above, after the graphene precursor is mixed with the sacrificial support, the mixture is reduced to produce a hybrid graphene nanosheet that incorporates the sacrificial particles as distinct elements within the nanosheet. According to some embodiments, the hybrid material may be thermally reduced. Reduction may be performed, for example in hydrogen gas at a temperature of between 250 and 1200 K for between 30 and 240 minutes.

After reduction, the hybrid GNS-sacrificial particle material can be ball-milled or subjected to high energy ultrasonic power to re-disperse and thus form a more uniform powder, if desired.

The sacrificial particles are then removed resulting in an amorphous, porous, 3D nanosheet. Removal of the sacrificial template particles may be achieved using any suitable means. For example, the template particles may be removed via chemical etching. Examples of suitable etchants include NaOH, KOH, and HF. According to some embodiments, HF may be preferred as it is very aggressive and can be used to remove some poisonous species from the surface of the material. Accordingly, those of skill in the art will be able to select the desired etchants based on the particular requirements of the supporting material being formed.

As a specific example, 3D-GNS materials were formed using the Sacrificial Support Method described above. A calculated amount of graphene oxide (2 g) was fully exfoliated in 100 ml of water using a high energy ultrasonic probe (the amount of energy delivered was 600 kJ). In a separate beaker, 5 g of silica (with a surface area 400 $m^2 \ g^{-1}$) was dispersed in 50 ml of water using an ultrasonic bath. The two colloidal solutions were then mixed together and ultrasonicated for 2 h in an ultrasonic bath. The water was evaporated at T=85 C for 12 h. The resulting solid hybrid $GO/SiO_2$ material was ball-milled at 400 RPM for 30 m. A final reduction of graphene oxide to GNS was performed at T=800 C, t=1 h in atmosphere of 7 at % of $H_2$. The silica was then removed by leaching with 25 wt % of HF overnight, the powder was then washed with DI water until neutral pH was achieved and dried at T=85 C overnight.

Figure 2:
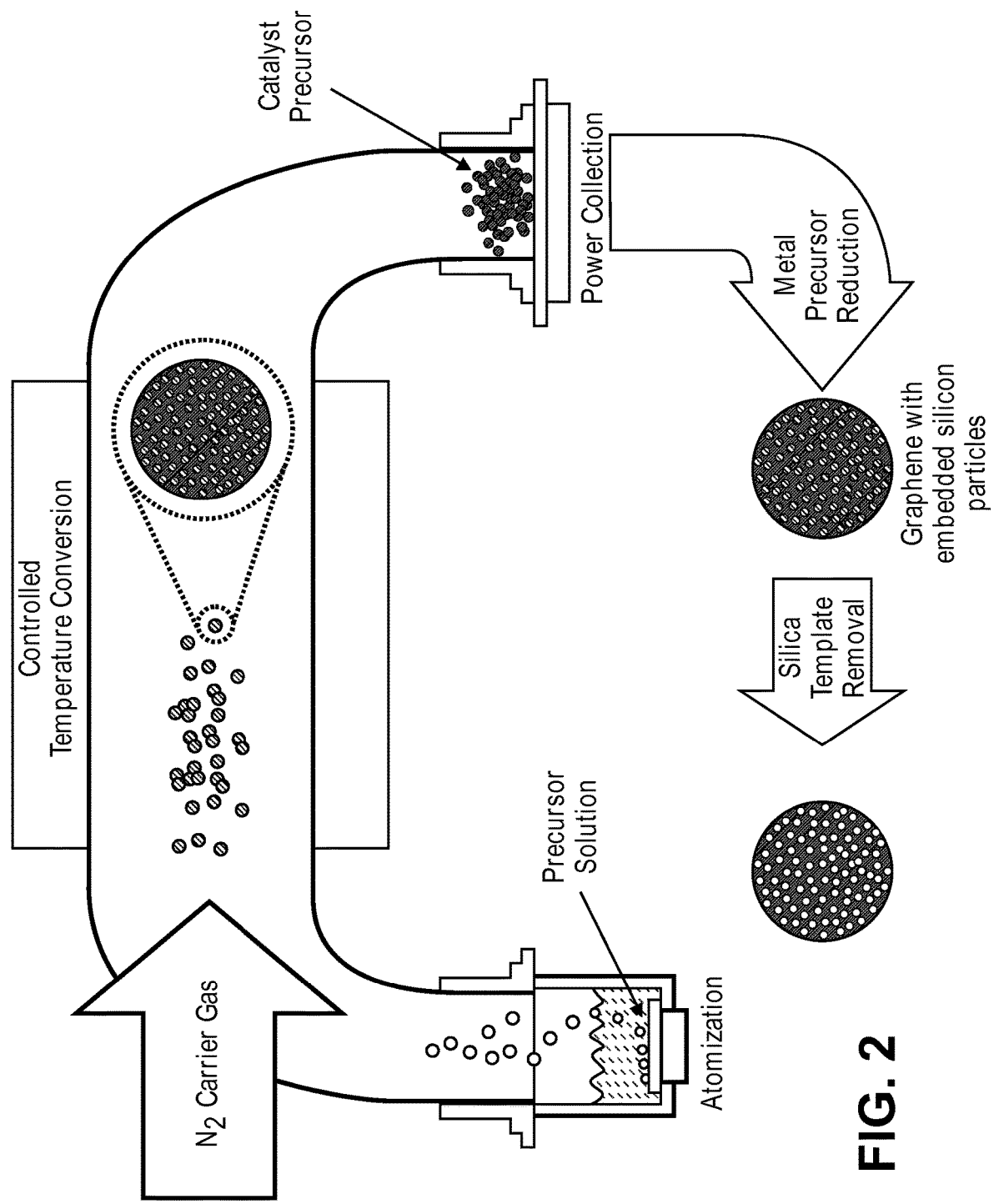
FIG. 2 is a schematic illustration of the steps of a spray pyrolysis-based method for producing 3D graphene flowers according to an embodiment of the present disclosure.

According to some embodiments it may be desirable to produce 3D-GNS materials that are spherical or nearly-spherical in shape. For example, as mentioned above, the hybrid materials of the presently disclosure may be used as the stationary phase for HPLC-based chiral separations. However, it will be understood that in some HPLC systems, it is desirable or typical that the stationary phase take the form of packed spheres (or "near-spheres"). Accordingly the present disclosure provides a method for forming 3D-GNS sphere-like shapes. As shown in FIG. 2, the 3D-GNS structures of the present disclosure can be formed by a combination of spray pyrolysis and the sacrificial template method described above. In this embodiment, graphene precursor(s) such as graphene oxide is dispersed on a sacrificial support as described above with respect to the sacrificial support method. The hybrid material is then atomized, for example, by use of an ultra-high power ultrasonic probe, and then transported by flowing inert/reactive/reductive gas through a pre-heated furnace. The supported graphene materials are then collected on a filter and heat treated. After heat treatment, the sacrificial support is removed, using the techniques described above.

Figure 3:
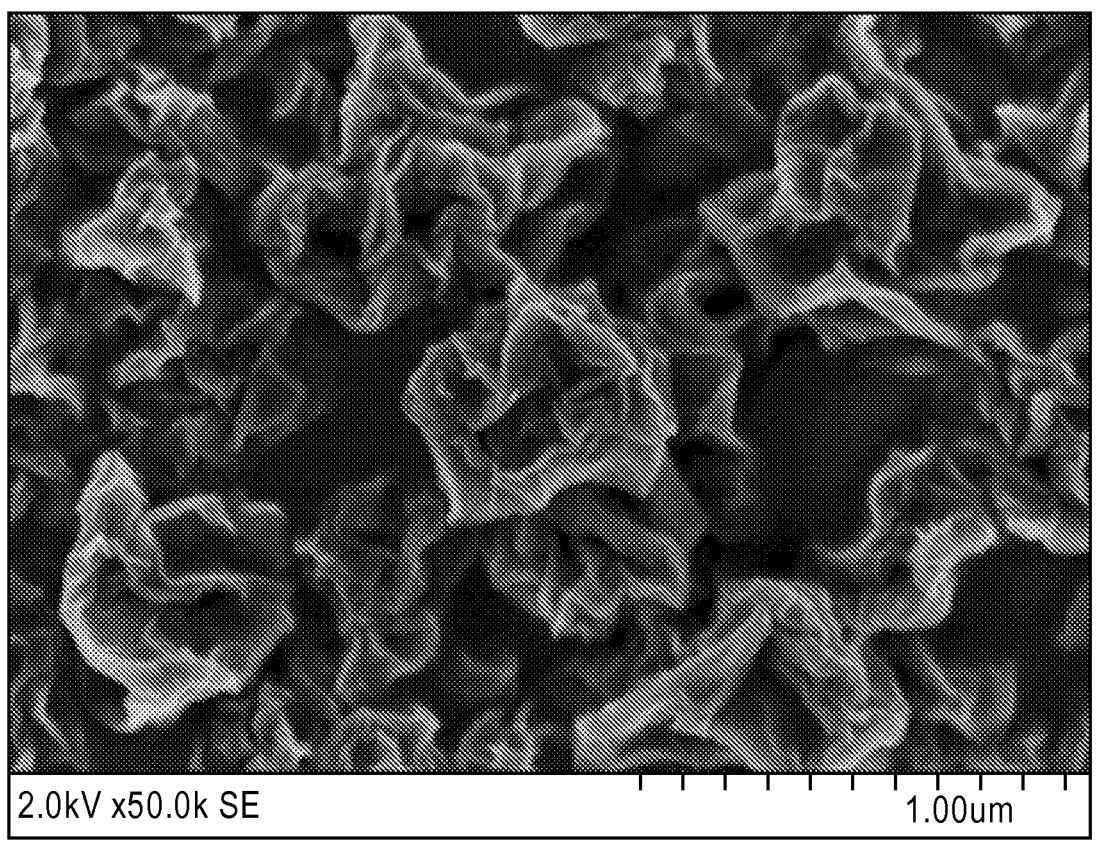
FIG. 3 is an illustration of the morphology of 3D graphene flowers that can be produced using the methods disclosed in the present disclosure.

The combined spray pyrolysis/sacrificial support method offers a fast and cost-effective method for producing large amounts of 3D graphene materials. FIG. 3 is a schematic illustration of the types of structures, referred to as "graphene flowers" that can be produced using this technique.

While much of the present disclosure is directed to the use of non-contiguous 3D GNS, it should be understood that the present disclosure contemplates a variety of different types of carbon and graphitic materials that could be modified using the methods described herein used for a variety of applications including, for example, the chiral separation applications described in greater detail below. Suitable types of carbon, graphene, and graphitic materials include, but are not limited to 3D GNS, 2D GNS, pristine graphite, carbon nanotubes, fullerenes, etc.

2D GNS can be prepared using know methods including, for example, chemical vapor deposition. Alternatively, 2D GNS can be prepared by chemical or thermal reduction of graphene oxide. For example, according to a specific embodiment, 5 g of $GO_x$ was dispersed in 100 ml of DI $H_2O$ by ultrasonic treatment with high energy probe. The resulting solution was heated to 85° C. and 150 ml of hydrazine hydrate (20 wt %) was added while stiffing on a magnetic stirrer. After 30 minutes, the color of the solution changed from brown to black and coarse particles of reduced graphene oxide precipitated. The resulting powder was filtrated, washed, and dried.

It should be understood that the 2D GNS or other types of graphitic materials can be altered to include defects, pits, and/or other malformations to increase surface area. For example, according to another embodiment, pristine graphite was ball-milled at 400 RPM for 2 hours resulting in formation of highly defective structure with medium surface are of 20 $m^2g^{-1}$.

As stated above, according to some embodiments, the graphene and or graphitic materials described above undergo covalent modification and attachment of a functional group.

The 2D/3D GNS or graphite-like materials described herein can be functionalized using any suitable procedure including, but not limited to, different types of cycloaddition, radical addition, functionalization using diazonium salts, organometallic functionalization, etc. It will be understood that the specific organic molecule bound to the 2D/3D GNS or graphite-like materials will be determined by the desired use for the material and therefore, the specific mechanism for attaching the organic molecule to the 2D/3D GNS or graphite-like materials will be determined by the attachment mechanisms that are available and/or necessitated by the structure and properties of the organic molecule and the material to which it will be attached.

According to an embodiment, 2D/3D GNS or graphite-like materials is modified with tetracyanoethylene oxide (TCNEO). In an example of an embodiment utilizing 3D-GNS, the 3D-GNS is heated with TCNEO for an appropriate amount of time (e.g., 48 hours) in chlorobenzene at a suitable temperature (e.g., 150-160° C.). It is noted that this is the first time chlorobenzene was used as a solvent and that this reaction time is significantly longer than previously described methodologies. The functionalized 3D-GNS is then removed and washed by different organic solvents, for example methanol, acetone, acetonitrile and others. Additional information regarding the modification of graphite or graphene materials with TCNEO may be found in L. V. Frolova, I. V. Magedov, A. Harper, S. K. Jha, M. Ovezmyradov, G. Chandler, J. Garcia, D. Bethke, E. A. Shaner, I. Vasiliev, N. G. Kalugin, Tetracyanoethylene oxide-functionalized graphene and graphite characterized by Raman and Auger spectroscopy, *Carbon* 81, January 2015, Pages 216-222, which is hereby incorporated by reference.

The functional groups attached to the 2D, 3D GNS or graphite-like materials can then act as enantiomer separators themselves or as anchors for an appropriate organic molecule. According to an embodiment, hydrolysis or reduction on the functionalized 2D, 3D GNS or graphite-like materials can be performed and then a desired organic molecule is bound for example, by ester bonding or amide bonding.

Figure 4:
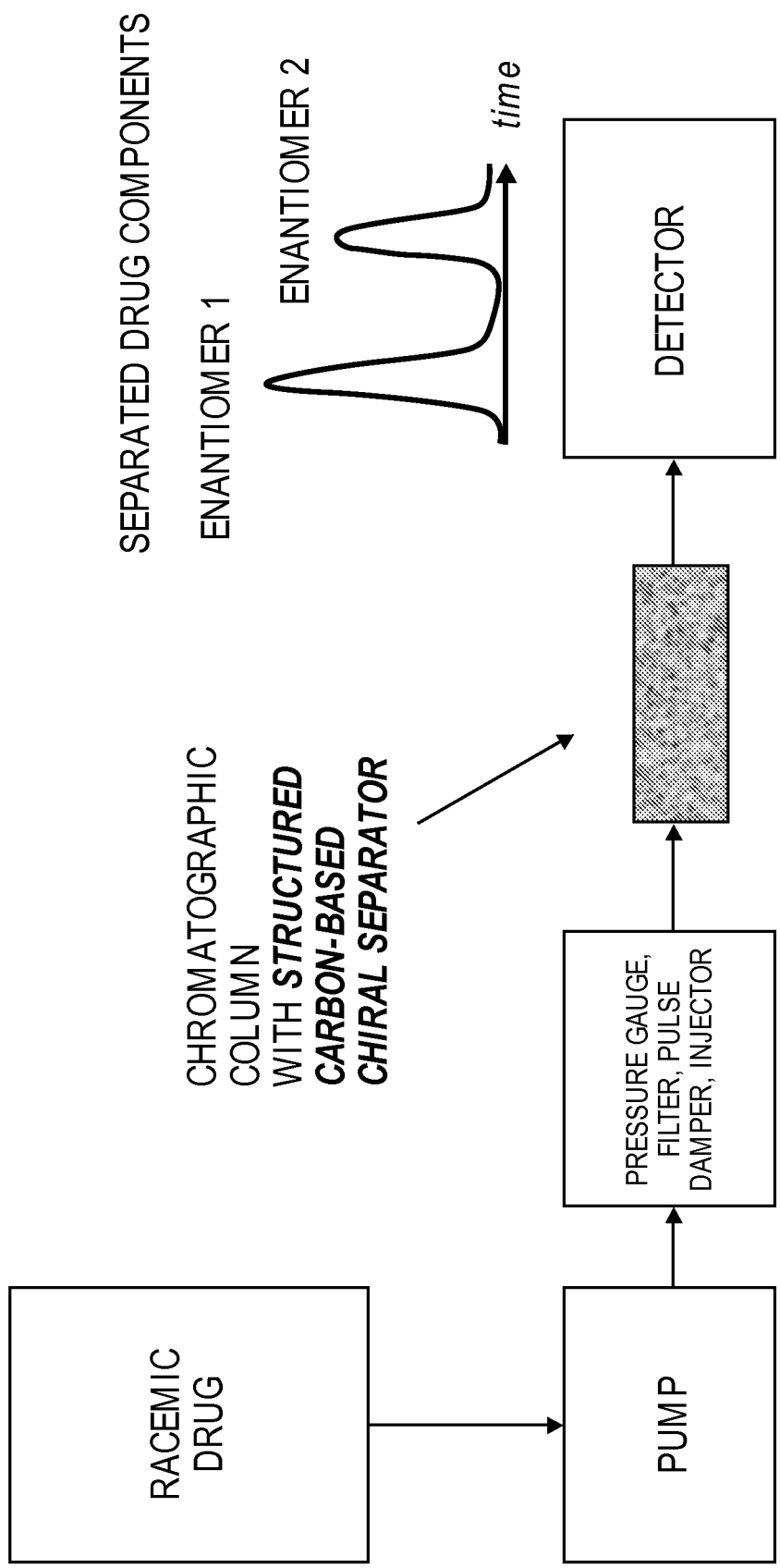
FIG. 4 is a schematic illustration of the steps for chiral separation of enantiomer according to an embodiment of the present disclosure.

According to various embodiments, the hybrid materials can the be used in various experiments including, but not necessarily limited to, those wherein the bound molecule selectively binds to a target molecule in a sample, making the hybrid material useful for a wide variety of separation and/or detection techniques. As stated above, according to a specific example, the bound molecule may selectively bind to one enantiomer of a chemical compound. For example, the hybrid materials of the present disclosure can easily be used as the stationary phase in HPLC-based chiral separations. A schematic of HPLC-based chiral separations is shown in FIG. 4. Briefly, an enantioselective molecule is bound to a hybrid material as described above. The enantiomers are then separated by flowing a racemic mixture through a chromatographic column. The presence of the enantioselective molecule on the hybrid material causes the different enantiomers to travel at different rates through the column, such that the first enantiomer exits the column ahead of the second enantiomer.

As a specific example, a hybrid 3D-GNS material as described above has been used for separation of ibuprofen enantiomers in racemic solutions. Ibuprofen is an optically active compound with both S- and R-isomers, with the S-isomer being more biologically active. In this particular example, the 3D-GNS was modified with TCNEO as described above. The TCNEO-modified hybrid material was then hydrolyzed and (S)-(+)-2-pyrrolidinemethanol attached via esterification (in this case (S)-(+)-2-pyrrolidinemethanol plays a role of enantiomer separator). In general, hydrolysis of the TCNEO cyanogroups can be performed by heating the modified material in acid and then washing in a base until neutral pH is achieved, followed by a second washing step and etherification. According to a specific example, 200 mg of modified material was heated in 7 ml of $H_2SO_4/H_2O$ (2/1 mixture) for 24 hours. The material was then filtered out and washed with $H_2O$ and $KHCO_3$ until reaching pH7. The material was subsequently washed with methanol, acetone, and acetonitrile and dried overnight. Etherification was performed by treating 200 mg of the hydrolyzed material with (S)-(+)-2-pyrrolidinemethanol in the presence of DMAP and DCC in dry methylene chloride under nitrogen for 3 days. Finally, the 3D-GNS hybrid was filtered, and washed with solutions of $KHCO_3$ and HCl, deionized H2O, methanol, acetone and acetonitrile. The proline-modified 3D-GNS material was then used as the substrate in a separation column and, separation of the R and S isomers was achieved, as confirmed by polarimetry measurements.

Examples of suitable racemic mixtures that would benefit from the type of enantiomeric separation described herein includes, but is not limited to, racemic mixes of organic acids (racemic mixture A), racemic mixture of organic bases, racemic mixtures of lipophilic molecules, racemic mixtures of lipophobic compounds which can be separated by hybrid material having enantiomer pure molecules attached as the enantiomer separators—

One of the advantages of the presently described system, is that the morphology of the 3D GNS hybrid can easily be modified as described above (for example, to increase or decrease surface area, porosity, tortuousness, etc.) so as to increase or decrease the density of the bound organic molecules, providing a mechanism for fine-tuning of the interactions between a target molecule and the bound molecule.

Furthermore, with regard to its ability to separate racemic mixtures, the 3D GNS material described herein has a very high capacity, our experiments demonstrated that 200 mg of modified material was able to separate 10 mg of racemic mixture of ibuprofen. Moreover, the hybrid material is highly durable allowing the use of a wide variety of solvents that are not available for use with currently existing commercially available racemic mixture separation preparations. These solvents include, but are not limited to, methylene chloride, methanol, and acetonitrile.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

What is claimed is:

1. An inorganic-organic hybrid material comprising a non-contiguous, three-dimensional graphene material comprising at least two layers of carbon atoms and comprising a plurality of voids wherein the graphene material is populated with organic molecules.

2. The inorganic-organic hybrid material of claim 1 wherein the organic molecule is an enantioselective molecule.

3. The inorganic-organic hybrid material of claim 2 wherein the enantioselective molecule is (S)-(+)-2-pyrrolidinemethanol.

4. The inorganic-organic hybrid material of claim 1, wherein the three-dimensional graphene structure is a plurality of graphene flowers wherein each graphene flower comprises a plurality of voids.

5. The inorganic-organic hybrid material of claim 4 wherein the three-dimensional structure is formed by:
dispersing a graphene precursor on a sacrificial support to produce a hybrid material;

atomizing the hybrid material;
flowing the atomized hybrid material through a pre-heated furnace to produce supported graphene materials;
collecting the supported graphene materials;
heat treating the collected supporting materials; and
removing the sacrificial support to produce voids.

6. The inorganic-organic hybrid material of claim 1 wherein the three-dimensional graphene material, comprises graphene walls and voids.

7. The inorganic-organic hybrid material of claim 6 wherein the voids are formed by the removal of a sacrificial support material.

8. The inorganic-organic hybrid material of claim 1 comprising a plurality of voids that have been formed by the removal of a sacrificial support material.

9. The inorganic-organic hybrid material of claim 1 wherein the three-dimensional shape is a sphere or near-sphere.

10. The inorganic-organic hybrid material of claim 9 wherein the sphere or near-sphere is formed by spray-pyrolysis.

11. The inorganic-organic hybrid material of claim 1 wherein the predetermined structure comprises pores of a predetermined shape or size.

12. The inorganic-organic hybrid material of claim 1, wherein the graphene comprises between 3 and 20 layers of carbon atoms.

\* \* \* \* \*